United States Patent [19]

Singer

[11] 4,219,673

[45] Aug. 26, 1980

[54] 2-(TRICHLOROMETHYLDITHIO)ACETIC ACID AND RELATED COMPOUNDS

[75] Inventor: Malcolm S. Singer, Novato, Calif.

[73] Assignee: Chevron Research Company, San Francisco, Calif.

[21] Appl. No.: 892,058

[22] Filed: Mar. 31, 1978

Related U.S. Application Data

[63] Continuation-in-part of Ser. No. 795,680, May 11, 1977, Pat. No. 4,110,475.

[51] Int. Cl.$^2$ .................... A61K 31/215; C07C 53/22
[52] U.S. Cl. ..................................... 562/602; 424/305
[58] Field of Search ......................... 562/602; 424/305

[56] References Cited

U.S. PATENT DOCUMENTS

| | | | |
|---|---|---|---|
| 2,553,778 | 5/1951 | Hawley | 424/311 |
| 3,595,915 | 7/1971 | Emerson et al. | 544/158 |

*Primary Examiner*—John M. Ford
*Assistant Examiner*—Robert C. Whittenbaugh
*Attorney, Agent, or Firm*—D. A. Newell; T. G. DeJonghe; R. J. Suyat

[57] ABSTRACT

In vivo and in vitro cellulose fermentation by cellulose-digesting microorganisms is increased by conducting the fermentation in the presence of a minor amount of a 2-(chloromethyldithio)acetic acid.

2 Claims, No Drawings

2-(TRICHLOROMETHYLDITHIO)ACETIC ACID AND RELATED COMPOUNDS

CROSS REFERENCE TO RELATED APPLICATION

This application is a continuation-in-part of application Ser. No. 795,680, filed May 11, 1977 now U.S. Pat. No. 4,110,475.

BACKGROUND OF THE INVENTION

The effect of chemical additives in microorganism fermentations has been extensively studied. For example, P. P. Williams et al, App. Microbiology, 11, 517 (1963) describe rumen bacteria and protozoal responses to insecticide substrate; J. J. O'Connor et al, J. Animal Sci., 33, 662 (1971) describe the in vivo effect of chemical additives on production of volatile fatty acids by rumen microorganisms; and L. W. Varner et al, J. Animal Sci., 33, 1110 (1971), describe the influence of ammonium salts upon rumen fermentation by steers; and T. W. Dowe et al, J. Animal Sci., 16, 93 (1957) describe the effect of corn treated with fungicides (N-trichloromethylthio-delta$^4$-tetrahydrophthalimide) on the performance of fattening steers.

PRIOR ART STATEMENT

U.S. Pat. No. 2,553,778 of Hawley discloses parasiticidal perchloromethylacetic acid esters. U.S. Pat. Nos. 3,442,941, 3,595,915, 3,629,313 and 3,718,687 of Emerson et al disclose pesticidal polyhaloethyl alkanoic acids. Although the compounds of these references are structurally related to the compounds of the invention, the compounds of the references have been found to be ineffective for increasing the rate of cellulose digestion by microorganisms.

DESCRIPTION OF THE INVENTION

The cellulose-fermentation-accelerating compounds of the invention are 2-(chloromethyldithio)acetic acid, 2-(dichloromethyldithio)acetic acid and 2-(trichloromethyldithio)acetic acid. The preferred compound is 2-(trichloromethyldithio)acetic acid.

The amount of compound employed in the process of invention depends in part upon the type of cellulosic material and the particular microorganism(s) employed. Generally, weight ratios of compounds to cellulosic matter in the range of about 1:10 to 1:1,000,000 are effective, although weight ratios in the range of about 1:100 to 1:10,000 are preferred.

In in vitro cellulose fermentation processes, the compound is generally added directly to the fermentation process. In in vivo cellulose digestion, the compound may be orally administered to the animal along with the cellulosic feedstuff. Alternatively, the cellulosic feedstuff may be pretreated with an effective amount of the compound prior to feeding the animal.

The process of the invention is generally applicable to in vivo or in vitro cellulose fermentation by microorganisms. Examples of in vitro cellulose fermentation by microorganisms are the aerobic and/or anaerobic destruction of cellulosic wastes in sewage plants; conversion of cellulose to sugar by microorganisms such as Trichoderma viride; conversion of cellulose to single-cell proteins by microorganisms such as Bacteroidaceae, Cellulomonas and Alcaliginis: and the biodegradation of lignincellulosic plant material. Examples of in vivo fermentation by microorganisms are cellulosic digestion by rumen microorganisms of ruminant animals, cecum microorganisms of animal intestines, and other cellulolytic organisms in the alimentary tracts of herbivores.

The process of the invention is suitably employed for all types of cellulosic material such as paper, municipal waste and plant products, e.g., wood, cotton, straw, bagasse, rice hulls, etc.

The process of the invention is particularly useful for increasing the digestion rate of cellulose by rumen microorganisms and for increasing the fermentation rate of cellulosic waste products by sewage microorganisms. Microorganisms commonly present in sewage sludge of sewage treatment plants include anaerobic and aerobic bateria such as Escherichia coli, Lactobacillus fermentans, Alcaligenes viscosus, Pseudomonas fluoresceus, Azotobachus chroococcum, Salmonella and Streptococcus.

EXAMPLES

Example 1—Cotton digestion by Bacteroides succinogenes

The organism, Bacteroides succinogenes, was obtained from the American Type Culture Collection, No. 19169.

| Nutrient Source: | Bacto-fluid Thioglycolate (29 g formulation/liter of H$_2$O) |
| --- | --- |
| | Bacto-Casitone 15.0 g |
| | Bacto-Yeast Extract 5.0 g |
| | Bacto-Dextrose 5.0 g |
| | NaCl 2.5 g |
| | 1-Cystine, Difco 0.5 g |
| | Thioglycolic Acid 0.3 ml |
| | Bacto-Agar Resazurin, Certified 0.001 g |

The rate of cotton digestion in the presence of several test compounds in the above nutrient broth with Bacteroides succinogenes was determined by the following procedure:

Cotton (100 mg) was placed in screw-cap tubes. To these the test compound (1 microgram) and the nutrient source (20 ml) were added to completely fill the tube.

The tubes were then sterilized, cooled and inoculated with the microbe (1 loop of inoculation needle), their caps tightened, and incubated in a water bath at about 40° C.

The tubes were stirred throughout incubation and the caps loosened every 2 hours for the first 18 hours and every 6 hours thereafter to release gases produced by the fermentation. After 70 hours of incubation, most of the fermentation processes had subsided, as noted by cessation of gas accumulation.

After various periods of incubation, the tubes were emptied on previously weighed filter paper. The filter paper was washed several times and dried to a constant weight. The weight of the undigested cotton was determined by difference.

The cellulose digestion results are tabulated in Table I. The results are based on the average of 48 runs and standard deviation analysis showed the results to be significant 1% level.

TABLE I

| Test Compound | Cotton Digestion % | Acceleration |
| --- | --- | --- |
| Control | 38.6% | — |
| 2-(trichloromethyldithio)- | 43.6% | 13% |

TABLE I-continued

| Test Compound | Cotton Digestion % | Acceleration |
|---|---|---|
| acetic acid | | |
| 2-(1,1,2,2-tetrachloroethyldithio)-acetic acid | 38.0% | 0 |

Example 2—Cotton digestion by *Bacteroides succinogenes*

The rate of cotton digestion with *Bacteroides succinogenes* in the presence of several test compounds was determined by a procedure identical to that of Example 1. The test compounds and the results are tabulated in Table II.

TABLE II

| Test Compound | Cotton Digestion % | Acceleration |
|---|---|---|
| Control | 37.1% | — |
| Methyl 2-(trichloromethyldithio)-acetate | 36.2% | 0 |
| Methyl 2-(1,1,2,2-tetrachloroethyldithio)acetate | 36.7% | 0 |

Example 3—Plant Cellulose Digestion by *Bacteroides succinogenes*

Lignin-cellulosic matter of herbaceous plant forage was digested by *Bacteroides succinogenes* in a purified medium in the presence of 2-(trichloromethyldithio)acetic acid at a concentration of 10 micrograms/ml by a procedure identical to that of Example 1. After 70 hours incubation, the percent cotton digestion was 54.3%. In an untreated control run, the percent cotton digestion was 41.1%.

This example exemplifies the in vitro separation of cellulose from lignin-cellulosic matter by biodegradation of the cellulose.

Example 4—Cotton Digestion by *Ruminococcus albus*

*Ruminococcus albus* was obtained from the America Type Culture Collection. It was cultured on Pseudomonas medium broth which contained the following (per liter of distilled $H_2O$):

| | |
|---|---|
| Nitrilotriacetic acid | 1.91 g |
| $K_2HPO_4$ | 8.71 g |
| $Na_2SO_4$ | 0.57 g |
| $MgSO_4$ | 0.25 g |
| $FeSO_4$ | 0.5 mg |
| $Ca(NO_3)_2$ | 0.5 mg |
| Agar | 1 g |

About 20 ml of the medium and 0.1 g cotton were added to each of 48 screw-cap tubes and sterilized. The tubes were then inoculated with 1 loopful of the microbe. To half of the tubes was added sufficient 2-(trichloromethyldithio)acetic acid to give a concentration of 10 micrograms per ml. The tubes were then sealed and incubated in a water bath for 70 hours at 40° C. At the end of the incubation period, the weight of undigested cotton was determined.

The treated tubes (average of 24) gave 29.8% cotton digestion. The control tubes (average of 24 gave 23.2% control.

Example 5—Cotton Digestion by *Bacteroides succinogenes* in rumen fluid

The rate of cotton digestion in the presence of 2-(trichloromethyldithio)acetic acid in sterilized rumen fluid with *Bacteroides succinogenes* was determined by a procedure identical to that of Example 1. After 70 hours incubation, the percent cotton digestion was 46.6%. In an untreated control run, the percent cotton digestion was 39.8%.

Example 6—Solka Floc digestion in rumen fluid

The effect of 2-(trichloromethyldithio)ecetic acid on the in vitro digestability of Solka Floc was determined using a modification of the two-stage digestion procedure (Tilley and Terry, J. Brit. Glassl. Sc. 18:104–111, 1963). Substrate (in triplicate) was treated with either 0, 40, 60, 80, 100 or 150 ppm of the test compound and incubated with buffered rumen fluid for 24 hours followed by 24 hours pepsin digestion. In vitro digestibility was measured at end of incubation with buffered rumen fluid (ruminal digestion) and at end of pepsin digestion (total digestion).

Rumen fluid was obtained from donor animal maintained on alfalfa hay—corn grain mineral supplement ration at maintenance plus level of intake. The test compound was added directly to Solka Floc on dry matter basis.

TABLE III

| Level of Test Compound[1] | Percent Ruminal Digestibility[2] | Percent Total Digestibility[2] |
|---|---|---|
| 0 ppm | 10.34 | 26.50 |
| 40 ppm | 13.96 (35.01) | 29.53 (11.43) |
| 60 ppm | 12.73 (23.11) | 30.00 (13.21) |
| 80 ppm | 13.18 (27.47) | 29.93 (12.94) |
| 100 ppm | 12.91 (24.85) | 29.16 (10.04) |
| 150 ppm | 11.96 (15.67) | 28.26 (6.64) |

[1]Values in parentheses represent percent increase.
[2]Test Compound added on substrate dry matter basis.

Example 7—Cottom digestion by sewage bacteria

The rate of cotton digestion in the presence of 2-(trichloromethyldithio)acetic acid in a bacto-fluid thioglycolate nutrient broth by anaerobic sewage bacteria was determined by the following procedure.

A nutrient broth was prepared by reconstituting a fluid thioglycolate mixture (same composition as that described in Example 1) with supernatant water obtained from a mixture of distilled water (70%) and raw sewage (30%) taken from a sludge digestion tank of a commercial sewage treatment plant. Twenty milliliters of the nutrient broth solution containing 10 micrograms of the test compound and 100 mg of cotton were placed in screw cap tubes (24 replicates). The tubes were innoculated with sewage bacteria by adding to the vial 0.5 ml of raw sewage sludge from the sewage treatment plant.

The tubes were closed and placed in a shaker, water bath maintained at 35° C. The caps were loosened every 2 hours for the first 6 hours of incubation and periodically thereafter at about 6 hour intervals to free accumulated gases of fermentation.

After 48 hours of incubation, the tubes were emptied on previously weighed filter paper. The filter paper was washed several times and dried to a constant weight. The weight of the undigested cotton was determined by difference.

The experiment (with 24 replicate tubes) was done with six different samples of sewage bacteria obtained every two weeks from the sewage treatment plant. The results for the six experiments are tabulated in Table IV. The fermentation rate was increased by an average of 60% in the presence of the test compound.

TABLE IV

| Level of test Compound | Cellulose Fermentation By Sewage Bacteria Experiment No. | | | | | | |
|---|---|---|---|---|---|---|---|
| | 1 | 2 | 3 | 4 | 5 | 6 | Average |
| 0 | 50.5% | 53.0% | 49.5% | 52.0% | 52.8% | 50.2% | 51.1% |
| 10 micrograms | 82.7% | 82.7% | 79.8% | 81.3% | 82.5% | 84.0% | 82.2% |

What is claimed is:

1. A compound selected from 2-(chloromethyldithio)acetic acid, 2-(dichloromethyldithio)acetic acid or 2-(trichloromethyldithio)acetic acid.

2. 2-(Trichloromethyldithio)acetic acid, according to claim 1.

* * * * *